(12) United States Patent
Leonard et al.

(10) Patent No.: US 7,897,194 B2
(45) Date of Patent: Mar. 1, 2011

(54) SYNERGISTIC SUPER POTENT ANTIOXIDANT COLD PRESSED BOTANIC OIL BLENDS

(75) Inventors: Arnold S. Leonard, Golden Valley, MN (US); Daniel A. Saltzman, Mendota Heights, MN (US); Mark J. Mueller, Spooner, WI (US)

(73) Assignee: Botanic Oil Innovations, Inc., Spooner, WI (US)

( * ) Notice: Subject to any disclaimer, the term of this patent is extended or adjusted under 35 U.S.C. 154(b) by 986 days.

(21) Appl. No.: 11/787,796

(22) Filed: Apr. 18, 2007

(65) Prior Publication Data

US 2007/0243310 A1    Oct. 18, 2007

Related U.S. Application Data

(60) Provisional application No. 60/792,763, filed on Apr. 18, 2006.

(51) Int. Cl.
    *A23D 9/00* (2006.01)
(52) U.S. Cl. .................................. 426/601; 426/542
(58) Field of Classification Search .................. 426/601
    See application file for complete search history.

(56) References Cited

U.S. PATENT DOCUMENTS

| | | | |
|---|---|---|---|
| 3,950,266 A | | 4/1976 | Chang et al. |
| 4,526,793 A | * | 7/1985 | Ingenbleek et al. ........... 426/72 |
| 4,938,984 A | * | 7/1990 | Traitler et al. ............... 426/580 |
| 4,970,235 A | * | 11/1990 | Traitler et al. ............... 514/558 |
| 5,009,891 A | | 4/1991 | Niwa et al. |
| 5,871,757 A | * | 2/1999 | Cloughley et al. .......... 424/401 |
| 6,251,441 B1 | * | 6/2001 | Van Den Braak et al. ....... 426/2 |
| 6,417,157 B1 | | 7/2002 | Wadsworth et al. |
| 6,444,242 B1 | * | 9/2002 | Skelbaek et al. .............. 426/98 |
| 6,579,512 B2 | * | 6/2003 | Crutchfield, III ............. 424/43 |
| 2005/0244375 A1 | | 11/2005 | Leonard et al. |
| 2007/0128301 A1 | * | 6/2007 | Saltzman et al. ............. 424/765 |
| 2007/0281044 A1 | * | 12/2007 | Mueller et al. ............... 424/727 |
| 2008/0107758 A1 | * | 5/2008 | Crutchfield, III ............ 424/732 |
| 2008/0260645 A1 | * | 10/2008 | Leonard et al. .............. 424/9.2 |

FOREIGN PATENT DOCUMENTS

WO    WO 00/32211    *    6/2000

OTHER PUBLICATIONS

Ustun, G et al. 1990. JAOCS 67(12)958.*
Parry, J. et al. 2004. Journal of Food Science 69(3)189.*
Atta, M. B. 2003. Food Chemistry 83:63.*
Ramadan, M. et al. 2004. Eur. J. Lipid Sci. Technol 106:35.*
Burits, M. et al. 2000. Phytotherapy Research 14:323.*
Wada, L. et al. 2002. J. Agric. Food Chem. 50:3495.*
Fruhwirth, G. 0. et al. 2003. Eur J. Lipid Sci Technol 105:266.*
Liu, M. et al. 2002. J. Agric Food Chem. 50:2926.*
Parry, J. et al. Journal of Food Science 69(3)189.*
T.D. Parker, D.A. Adams, K. Zhou, M. Harris, L. Yu; Fatty Acid Composition and Oxidative Stability of Cold-pressed Edible Seed Oils; Journal of Food Science; vol. 68, No. 4, pp. 1240-1243; Institute of Food Technologists 2003.

* cited by examiner

*Primary Examiner*—Carolyn A Paden
(74) *Attorney, Agent, or Firm*—Gerald E. Helget; Nelson R. Capes; Briggs and Morgan, P.A.

(57) ABSTRACT

A composition of cold pressed botanic oils exhibiting antioxidant activity. The composition is a combination of at least two oils, which can be black cumin oil, black raspberry oil, red raspberry oil, pomegranate oil, pumpkin oil, or sesame, flax, chardonnay grape seed oil or any other fruit, herb, vegetable, grain or nut oil. The composition exhibits total antioxidant activity greater than the sum of the weighted average of the antioxidant activities of the individual oils. A method of producing a composition of botanic oils exhibiting antioxidant activity, comprising extracting oil in an oxygen deprived environment from fruits and vegetables and combining the extracted oils. The composition exhibits total antioxidant activity greater than the sum of the weighted average of the antioxidant activities of the individual oils.

18 Claims, 1 Drawing Sheet

SYNERGISTIC SUPER POTENT ANTIOXIDANT COLD PRESSED BOTANIC OIL BLENDS

CROSS-REFERENCE TO RELATED APPLICATION

The present application is based on and claims the benefit of U.S. provisional patent application Ser. No. 60/792,763, filed Apr. 18, 2006, the content of which is hereby incorporated by reference in its entirety.

BACKGROUND OF THE INVENTION

Free radicals are atoms or molecules with open negative charges that are capable of damaging the human body. Free radicals are produced by dietary imbalances, pollutants, or from inflammation and biochemical reactions in the body that can increase the probability of viral or bacterial infections or cancer.

Long-term presence of these oxidizing radicals can eventually be detrimental to the human body. Oxidative stress is also thought to play an important role in numerous chronic diseases, such as coronary heart disease and cancer. Although there are many factors in the development of these diseases, considerable experimental evidence has linked the production of free radicals to biologic damage that can provide a basis for the beginning and progression of certain diseases. When free radicals exceed the body's capacity to protect or repair itself, oxidative damage can occur.

Antioxidants, which reduce oxidative stress, may play a role in the prevention or treatment of many diseases. The accumulation and growth of free radicals in the body are often found in association with a suppressed immune system, including infections such as HIV, SARS, cancer and heart disease. Damage to the heart has been shown to be reduced with increased dietary antioxidant intake. Diets high in added antioxidants have been shown to be protective against cancer and various diseases experimentally.

Plant seed oils that can be extracted from the fruit, leaves, or seeds of various plants have been found to be a source of antioxidants. However, over-the-counter plant oils, such as canola, sesame, flax and sunflower, have low antioxidant values when compared to this invention. In addition to traditional antioxidants, such as vitamins C and E, some plant oils contain phenolic compounds which are excellent free radical scavengers due to their electron structure.

SUMMARY OF THE INVENTION

Combinations of cold pressed plant seed oils chosen from the group comprising black cumin, black raspberry, red raspberry, pomegranate, pumpkin, flax, sesame and chardonnay grape, when blended, provide synergistic super antioxidant values expressed in Trolox equivalents significantly greater than weighted arithmetic average values of the blends.

Synergistic super antioxidant plant seed oil blends may be orally taken to reduce free radicals in the body.

Synergistic super antioxidant plant seed oil blends are believed to prevent diseases, cure diseases and prolong life and slow the aging process.

DETAILED SPECIFICATION

Figure 1:
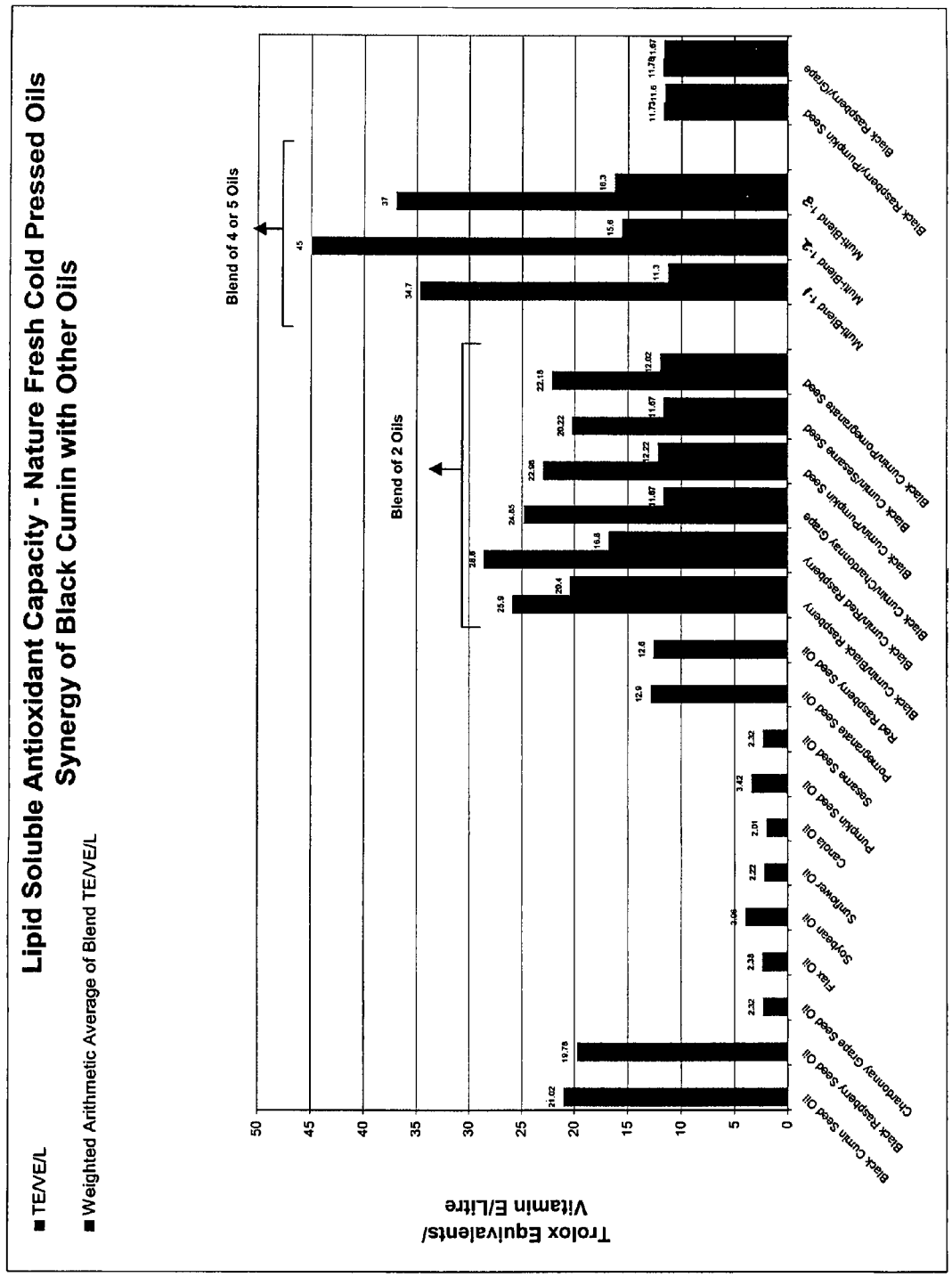
FIG. 1 is a graph showing the ORAC values of many single and blended botanic oils.

Cold pressed oils, when extracted at temperatures below 100° F. and when extracted in an oxygen deprived environment, yield excellent quality oils compared to traditional high temperature extraction methods. When using cold pressing, nothing is added to the seed or to the oil. The oils are potent, pure and unadulterated.

Without solvents, bleaching agents or high temperatures, these botanical seeds release their nutrient-dense oil containing a diverse array of nutrients including Omega 3 essential fatty acids and potent antioxidants. Oils produced by this cold press process may accelerate the activity of the immune system, and thus could moderate the aging process.

Other methods of extraction include use of heat, solvents and enzymes. These methods typically alter, damage or destroy some or all the antioxidants in the natural oils. Super critical carbon dioxide extraction method is known to produce a high quality oil comparable to cold pressing but is a more expensive process than cold pressing.

ORAC (Oxygen Radical Absorption Capacity) values represent the total antioxidant measurement of these oils, individually and blended, and demonstrate the potency created by the cold press process. Lab data (FIG. 1: graft) created by applicants at the University illustrate this.

FIG. 1 shows a chart of antioxidant values of the cold pressed oils using a Photochem® analyzer by Analytik Jena A.G. of Jena, Germany measuring instrument. The instrument is able to measure antioxidant values expressed in Trolox Equivalents of Vitamin E per Liter (TE/VE/L) in different botanical oils.

Typical antioxidant values for common food vegetable oils such as flax oil, soybean oil, canola oil, and grape seed oil are 2.38 TE/VE/L, 3.96, 2.01 and 2.32 respectively.

Potent antioxidant botanical oils, however, such as black raspberry seed oil and black cumin oil have values 19.78 TE/VE/L and 21.02 respectively, a factor of 9 to 10 times greater than common vegetable oils. Other known potent antioxidant seed oils are red raspberry, sea berry, cranberry, mullein and black berry, to mention a few.

This invention is a method of creating a composition of botanic oils causing synergy and resulting in super potent antioxidant levels even greater than 9 to 10 times that of common vegetable oils. Combining black cumin oil with other oils causes an unexpected outcome resulting in an antioxidant level that is greater than the sum of the weighted average of the antioxidant level of the individual component oils. Applicants believe black cumin seed oil chelates other botanic oils to release antioxidant bonds to transition metals and releases more antioxidants.

For example, when black cumin oil (21.02 TE/VE/L) is blended with the grape seed oil (2.32 TE/VE/L) in a 50:50 ratio, the arithmetic average of antioxidant value of the composition is 11.67 TE/VE/L. However, the Photochem® instrument analysis demonstrates a phenomena of synergy whereby the actual antioxidant value of this combination of black cumin oil and grape seed oil in a 50:50 ratio is 24.85 TE/VE/L. Other examples of synergistic compositions as shown in the FIG. 1 chart are:

TABLE 1

| Compositions of 50:50 ratio | Arithmetic value TE/VE/L | Synergistic Actual Value TE/VE/L |
| --- | --- | --- |
| Black Cumin/Black Raspberry Seed Oil | 20.4 | 25.90 |
| Black Cumin/Red Raspberry Seed Oil | 16.82 | 28.57 |
| Black Cumin/Pomegranate Seed Oil | 16.96 | 22.15 |
| Black Cumin/Pumpkin Seed Oil | 12.22 | 22.98 |

TABLE 1-continued

| Compositions of 50:50 ratio | Arithmetic value TE/VE/L | Synergistic Actual Value TE/VE/L |
|---|---|---|
| Black Cumin/Sesame Seed Oil | 11.67 | 20.22 |
| Black Cumin/Grape Seed Oil | 11.67 | 24.85 |
| Black Cumin/Flax Seed Oil | 12.19 | 22.00 |

Even greater synergistic antioxidant levels can be created through blends or compositions of more than two oils. Multi-blend compositions of four or five oils have the following values as illustrated in the FIG. 1 chart:

TABLE 2

| | | Weighted Average of Composition | Synergistic Actual Value |
|---|---|---|---|
| Blend #1-1 | Black Cumin(37.5%) Grape(37.5%) Black Raspberry(5%) Pumpkin(10%) Red Raspberry(10%) | 11.3 | 34.7 |
| Blend #1-2 | Black Cumin(65%) Grape(20%) Black Raspberry(5%) Pumpkin(10%) | 15.6 | 45 |
| Blend #1-3 | Black Cumin(65%) Grape(7.5%) Black Raspberry(5%) Pumpkin(15%) Red Raspberry(7.5%) | 16.3 | 37 |

Used properly, these oils and others produced by the cold press method should be advantageous in the support of the immune system and in certain problems where inflammation occurs. Recent laboratory observations (FIG. 1 chart) have demonstrated synergism with a number of oils by markedly increasing the measured antioxidant capacity especially when black cumin oil, for example, is paired with several oils. The antioxidant levels are increased over the expected weighted average. Also, when more than two oils are added to the black cumin natural processed oil, an even higher antioxidant level occurs than would be expected—again by the weighted average. These super concentrated antioxidants can prevent many diseases and aging processes from progressing.

Multiple antioxidants are better than single antioxidants—an observation known. However, synergy has been created and demonstrated by applicants and proven in their lab results (FIG. 1 chart). The "timing" of the immune system and neutralization of free radicals by this important observation producing higher concentrations of well recognized nutrients may help moderate the aging process, accelerate modulation of the immune system and thus affect a number of diseases produced by gradual increase in free radicals.

It is important to also recognize the overall value of black cumin oil in this process. This oil contains thymoquinone, has been shown to stimulate the production of prostaglandins E1, the modulator of the immune T cell response. Black raspberry oil also modulates the immune response by increasing T8 and NK cells in a colon cancer model at the University of Minnesota (see co-owned U.S. Published Patent Application 2005/0244375). What also is important to recognize is that the oils sold over the counter, such as canola, sesame seed, flax, and sunflower, have low antioxidant values when compared to the cold press oils with synergism. Clinical trials are underway to evaluate these observations.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described below. All publications, patent applications, patents, and other references mentioned herein are incorporated by reference in their entirety to the extent allowed by applicable law and regulations. In case of conflict, the present specification, including definitions, will control.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A composition of at least two cold pressed botanic oils having antioxidant properties, comprising black cumin oil and a botanic oils selected from the group consisting of black raspberry oil, red raspberry oil, pomegranate oil, pumpkin oil and chardonnay grape oil, wherein the composition exhibits total antioxidant activity greater than the arithmetic average of the antioxidant activity of the botanic oils.

2. The composition of claim 1, wherein the botanic oils are derived from seeds being cold pressed in an oxygen deprived environment at a temperature less than about 100° F.

3. The composition of claim 1, comprising two botanic oils in a 50:50 ratio.

4. The composition of claim 3, wherein the ratio of total antioxidant activity of the composition to the arithmetic average of the antioxidant activity of the two botanic oils is in the range of about 1.2 to about 2.1.

5. The composition of claim 1, comprising at least three botanic oils.

6. The composition of claim 5, wherein the composition exhibits total antioxidant activity greater than the sum of the weighted average of the antioxidant activity of the individual botanic oils.

7. The composition of claim 1, wherein the black cumin oil is present in a range of about 37.5% to about 65%.

8. The composition of claim 7, wherein the ratio of total antioxidant activity of the composition to the sum of the weighted average of the antioxidant activity of the individual botanic oils is in the range of about 2.3 to about 3.1.

9. A method of producing a composition of cold pressed botanic oils from seeds having antioxidant properties, comprising extracting oil in an oxygen deprived environment at a temperature less than about 100° F. from black cumin and a botanic oil selected from the group consisting of black raspberry, red raspberry, pomegranate, pumpkin, sesame and chardonnay grape and combining the extracted oils, wherein the total antioxidant activity of the composition is greater than the sum of the weighted average of the antioxidant activity of the individual oils.

10. The composition of claim 9, comprising two botanic oils.

11. The composition of claim 10, comprising two botanic oils in a 50:50 ratio.

12. The composition of claim 11, wherein one of the two botanic oils is black cumin oil.

13. The composition of claim 12, wherein the ratio of total antioxidant activity of the composition to the arithmetic average of the antioxidant activity of the two botanic oils is in the range of about 1.2 to about 2.1.

14. The composition of claim 9, comprising more than two botanic oils.

15. The composition of claim 9, wherein the black cumin oil is present in a range of about 37.5% to about 65%.

16. The composition of 15, wherein the ratio of total antioxidant activity of the composition to the sum of the weighted average of the antioxidant activity of the individual botanic oils is in the range of about 2.4 to about 3.1.

17. A composition of at least two cold pressed botanic oils having antioxidant properties, comprising black cumin oil and at least three other botanic oils selected from the group consisting of black raspberry oil, red raspberry oil, pomegranate oil, pumpkin oil and grape oil, wherein the composition exhibits total antioxidant activity greater than the arithmetic average of the antioxidant activity of the botanic oils.

18. The composition of claim 17, wherein the botanic oils are derived from seeds being cold pressed in an oxygen deprived environment at a temperature less than about 100° F.

\* \* \* \* \*